(12) United States Patent
Ying et al.

(10) Patent No.: US 6,489,258 B1
(45) Date of Patent: Dec. 3, 2002

(54) SYNTHESIS AND APPLICATION OF VAPOR GRAFTED POROUS MATERIALS

(75) Inventors: Jackie Y. Ying, Winchester, MA (US); Christian P. Mehnert, Clinton, NJ (US)

(73) Assignee: Massachusetts Institute of Technology, Cambridge, MA (US)

(*) Notice: Subject to any disclaimer, the term of this patent is extended or adjusted under 35 U.S.C. 154(b) by 0 days.

(21) Appl. No.: 09/419,365

(22) Filed: Oct. 15, 1999

Related U.S. Application Data

(63) Continuation of application No. PCT/US98/07354, filed on Apr. 15, 1998.
(60) Provisional application No. 60/042,232, filed on Apr. 15, 1997.

(51) Int. Cl.[7] .......................... B01J 31/16; C07C 67/03; C07C 5/42
(52) U.S. Cl. .............................. 502/60; 502/64; 502/72; 585/657; 585/659; 560/92; 560/217
(58) Field of Search .............................. 502/60, 64, 74, 502/72; 585/659, 657; 560/92, 217

(56) References Cited

U.S. PATENT DOCUMENTS 5,026,673 A    6/1991 Gates et al. ................... 502/62

(List continued on next page.)

FOREIGN PATENT DOCUMENTS

| EP | 0 438 131 A1 | 7/1991 |
| EP | 0 564 919 A1 | 10/1993 |
| EP | 0 569 268 A1 | 11/1993 |
| EP | 0 584 043 A1 | 3/1994 |
| EP | 0 589 679 A2 | 3/1994 |
| EP | 0 749 781 A2 | 12/1996 |
| WO | WO 98/17389 | 4/1998 |

OTHER PUBLICATIONS

Okamoto et al., J. Phys. Chem., vol. 95, pp. 3700–3705, 1997.*
P. Schmidt–Winkel et al., "Mesocellular Siliceous Foams with Uniformly Sized Cells and Windows," J. Am. Chem. Soc., vol. 121, No. 1, pp. 254–255, 1999.
E. Lindner et al., "Chemistry in Interphases–A New Approach to Organometallic Syntheses and Catalysis," Angew. Chem. Int. Ed., vol. 38, pp. 2154–2174, 1999.
D. Zhao et al., "Triblock Copolymer Syntheses of *Mesoporous silica* with Periodic 50 to 300 Angstrom Pores," Science, vol. 279, pp. 548–552, Jan. 23, 1998.
C. Amatore et al., "Intimate Mechanism of Oxidative Addition to Zerovalent Palladium Complexes in the Presence of Halide Ions and Its Relevance to the Mechanism of Palladium–Catalyzed Nucleophilic Substitutions," J. Am. Chem. Soc., vol. 115, No. 21, pp. 9531–9541, 1993.
Y. Ben–David et al., "Palladium–Catalyzed Vinylation of Aryl Chlorides. Chelate Effect in Catalysis," Organometallics, vol. 11, No. , pp. 1995–1996, 1992.

(List continued on next page.)

*Primary Examiner*—Porfirio Nazario-Gonzalez
(74) *Attorney, Agent, or Firm*—Wolf, Greenfield & Sacks, P.C.

(57) ABSTRACT

This invention provides an article, compositions, methods of making and uses of vapor-deposited metal compounds immobilized on porous substrates. The substrate is a porous substrate having an average pore size of at least about 8 Å and a surface area of at least about 10 m²/g. The methods describe the vapor-deposition of an inorganic compound onto the substrate where the deposition is accomplished with a relatively small amount of ligand loss. The substrate can be pre-treated to achieve a uniformly dispersed metal compound deposited on the substrate. The inorganic compound can decompose into a metal compound. The article can also function as a catalyst for carbon-heteroatom coupling reactions such as carbon-carbon coupling reactions, most notably, the Heck reaction.

24 Claims, 11 Drawing Sheets

U.S. PATENT DOCUMENTS

| | | |
|---|---|---|
| 5,145,816 A | 9/1992 | Beck et al. ............... 502/60 |
| 5,200,058 A | 4/1993 | Beck et al. ............... 208/46 |
| 5,215,950 A | 6/1993 | Bournonville et al. ...... 502/66 |
| 5,229,410 A | 7/1993 | Flaugh et al. ............. 514/411 |
| 5,296,428 A | 3/1994 | Degnan et al. ............ 502/84 |
| 5,365,000 A | 11/1994 | Kresge et al. ............. 585/407 |
| 5,389,595 A | 2/1995 | Simpson et al. ........... 502/315 |
| 5,391,528 A | 2/1995 | Benazzi et al. ............ 502/66 |
| 5,396,016 A | 3/1995 | Jablonski et al. .......... 585/708 |
| 5,399,259 A | 3/1995 | Dai et al. ............... 208/216 PP |
| 5,413,984 A | 5/1995 | Marecot et al. ............ 502/333 |
| 5,456,822 A | 10/1995 | Marcilly et al. ........... 208/136 |
| 5,476,596 A | 12/1995 | Kurek ..................... 210/763 |
| 5,487,918 A | 1/1996 | Akhtar .................... 427/255.3 |
| 5,489,722 A | 2/1996 | Resasco et al. ............ 585/661 |
| 5,492,964 A | 2/1996 | Tour et al. ............... 524/781 |
| 5,523,506 A | 6/1996 | Benazzi et al. ............ 585/481 |
| 5,538,931 A | 7/1996 | Heinrichs et al. .......... 502/234 |
| 5,540,981 A | 7/1996 | Gallagher et al. .......... 428/220 |
| 5,591,797 A | 1/1997 | Barthel et al. ............ 524/493 |
| 5,641,723 A | 6/1997 | Bonnemann et al. ......... 502/326 |
| 5,652,192 A | 7/1997 | Matson et al. ............. 502/304 |
| 5,661,097 A | 8/1997 | Spencer et al. ............ 502/115 |

OTHER PUBLICATIONS

R.P. Hughes & D.S. Tucker, "$\eta^3$–Cyclopropenyl Is Isolobal with NO, but Not with $\eta^3$–Propenyl (Allyl): Evidence from Conformational Preferences and Rotational Barriers in Alkene and Alkyne Complexes of Iridium," Organometallics vol. 12, No. 12, pp. 4736–4738, 1993.

M. Portnoy et al., "Clarification of a Remarkable Chelate Effect Leads to Palladium–Catalyzed Base–Free Olefin Arylation," Organometallics, vol. 12, No. 12, pp. 4734–4735, 1993.

W.A. Herrmann et al., "Metal Complexes of N–Heterocyclic Carbenes—A New Structural Principle for Catalysts in Homogeneous Catalysis," Angew. Chem. Int. Ed. Engl., Communications, vol. 34, No. 21, pp. 2371–2374, 1995.

C. Amatore et al., "Evidence for the Ligation of Palladium (0) Complexes by Acetate Ions: Consequences on the Mechanism of Their Oxidative Addition with Phenyl Iodide and PhPd(OAc)(PPh$_3$)$_2$ as Intermediate in the Heck Reaction," Organometallics, vol. 14, No. 12, pp. 5605–5614, 1995.

J. Louie & J.F. Hartwig, "A Route to Pd$^0$ from Pd$^{11}$ Metallacycles in Amination and Cross–Coupling Chemistry," Angew. Chem. Int. Ed. Engl., Communications, vol. 35, No. 20, pp. 2359–2361, 1996.

J.T. Richardson, Principles of Catalyst Development, Plenum Press publisher, Chapter 6.4 Depositon of the Active Components, pp. 108–120, 1989.

C.P. Mehnert & J. Y. Ying, "Palladium–grafted mesoporous MCM–41 material as heterogeneous catalyst for Heck reactions," Chem. Commun., pp. 2215–2216, 1997.

* cited by examiner

50 nm

SYNTHESIS AND APPLICATION OF VAPOR GRAFTED POROUS MATERIALS

This application is a continuation of co-pending application Ser. No. PCT/US98/07354, filed Apr. 15, 1998, entitled Synthesis and Application of Vapor Grafted Porous Materials, which claims priority to and is a continuation-in-part of U.S. provisional application Ser. No. 60/042,232, filed Apr. 15, 1997.

FIELD OF THE INVENTION

This invention provides an article comprising a vapor-deposited metal compound immobilized on a porous substrate. The invention also provides methods for depositing the metal compound. The article can also function as a catalyst for carbon-heteroatom coupling reactions such as carbon-carbon coupling reactions, most notably, the Heck reaction.

1. Background of the Invention

High-surface-area, porous substrates are of great interest in the field of catalysis. In particular, substrates with large and uniform pore sizes allow sterically-hindered molecules easy diffusion to internal active sites. Typically, catalytic species are immobilized within pores of porous substrates by depositing a catalyst from solution within pores of the substrate. In general, it is a challenge in the art to provide good deposition techniques for secure immobilization of catalysts on porous substrates, and the fabrication of substrates having large pore sizes has in many cases been challenging. It is among the objects of the present invention to provide techniques for secure immobilization of species on porous substrates, articles produced thereby, and methods of reactive chemistry using such articles.

2. Discussion of Related Art

U.S. Pat. No. 5,391,528 (Benazzi, et al.) describe deposition, from vapor, from organometallic compounds onto alumino-silicates.

U.S. Pat. No. 5,641,723 (Bonnemann, et al.) describe a technique for preparing highly-active doped supported catalysts from an organic or inorganic support material and a catalyst metal precursor. Deposition occurs from solution phase.

SUMMARY OF THE INVENTION

The invention provides methods of making surface-immobilized, metal-based catalysts, articles that can be useful for catalyzing organic reactions, and catalytic reactions involving metal-based catalysts.

According to one aspect, the invention involves methods of making articles. One method involves volatilizing an inorganic compound, and allowing the inorganic compound to become immobilized on a porous oxygen-containing substrate. The immobilization occurs to the extent that it is immobilized under sublimation conditions.

Another method of the invention involves pretreating a substrate having a plurality of chemically active sites of a first chemical functionality such that about 1–25% of the sites retain the first chemical functionality and about 75–99% of the sites have a second functionality. The sites retaining the first chemical functionality are uniformly dispersed. An inorganic compound then is volatilized to cause it to covalently bond to the pretreated substrate.

Another method of the invention involves providing a porous substrate having an average pore size of at least about 8 Å and depositing a metal compound on the substrate. Then, a carbon-heteroatom coupling reaction is carried out involving the metal compound.

Another method of the invention involves performing a carbon-heteroatom coupling reaction in air, wherein at least about 5% conversion, of the reaction, is achieved within about 1 h.

Another method of the invention involves carrying out a reaction catalyzed by a surface-immobilized catalyst having a surface area of at least about 50 $m^2/g$, in air, at a temperature of at least about 50° C. Catalyst degradation, defined by reduction of activity of catalysts, is allowed in an amount of less than about 30% of a period of time of at least about 1 h.

In another aspect the invention involves compositions and articles. One composition of the invention comprises the structure SUBSTRATE—O—M—$L_x$, wherein a bond between O and M is a covalent bond.

In another embodiment an article is provided that comprises a vapor-deposited metal compound immobilized on a porous substrate. The substrate has an average pore size of at least about 8 Å.

Other advantages, novel features, and objects of the invention will become apparent from the following detailed description of the invention when considered in conjunction with the accompanying drawings, which are schematic and which are not intended to be drawn to scale. In the figures, each identical or nearly identical component that is illustrated in various figures is represented by a single numeral. For purposes of clarity, not every component is labeled in every figure, nor is every component of each embodiment of the invention shown where illustration is not.

BRIEF DESCRIPTION OF THE DRAWINGS

FIG. 7(a) is a photocopy of a transmission electron micrograph (TEM) image of a hexagonally-packed pore structure in Pd-TMS11 and 7(b) shows a higher magnification;

FIGS. 8a–8e are photocopies of energy dispersive analysis by x-ray (EDAX) study conducted on Pd-TMS11 particles, in which FIG. 8a is an image, FIG. 8b is an oxygen map, FIG. 8c is a silicon map, FIG. 8d is a palladium map, and FIG. 8e is an image and palladium overlay;

DETAILED DESCRIPTION

Figure 1:
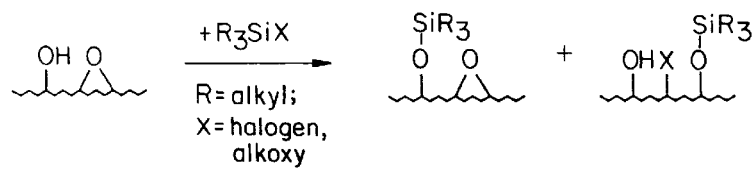
FIG. 1 depicts a schematic showing pretreatment of a surface with $R_3SiX$.

One aspect of the invention provides a method for synthesizing a material prepared by depositing a metal compound onto a substrate. The method allows deposition of various metal compounds onto substrates through a unique deposited inorganic compound intermediate. A primary use for these materials is as a heterogeneous catalyst. The method allows the formation of a wide variety of materials through judicious choice of metals, substrates and substrate dimensions.

The present invention involves deposition of a material, typically a metal compound, or an inorganic compound, onto substrate surfaces that need not be heated to temperatures typically associated with known chemical vapor deposition techniques. In typical chemical vapor deposition techniques, a vaporized precursor is exposed to a significantly-heated substrate at which ligand loss of the precursor occurs immediately at the substrate to cause deposition of one or more metals at the surface. For example, an organometallic precursor may be exposed to a heated substrate and lose essentially 100 weight percent of its ligands at the substrate to cause deposition of the metal, optionally in combination with other materials. The present invention involves deposition of a material without significant ligand loss. In particular, a precursor is exposed to a substrate surface and less than about 50 wt % of ligands are lost as the precursor is deposited on the surface. Preferably less that about 30 wt % of ligands are lost are lost in the process, more preferably less than about 20 wt %. This occurs via deposition on a substrate surface at a substrate temperature of preferably less than about 280° C., more preferably less than about 175° C., and in other embodiments less than 100° C. In some embodiments the substrate can be kept at a temperature of less than 60° C. during deposition.

The deposition method involves providing an inorganic compound in the gas phase such that a first step of the method involves volatilizing the inorganic compound. The inorganic compound can include an organometallic compound having at least one metal-carbon bond, a coordination compound where at least one ligand bonds to a metal ion, or any combination thereof. The metal is selected from the group consisting of alkali metals, alkaline earth metals, main group metals, transition metals, actinides, and lanthanides. Preferably, the inorganic compound is stable to sublimation, namely its structure prior to entering the vapor phase is the same as the structure obtained after entering the vapor phase and resolidifying i.e. sublimation.

The method further comprises depositing the volatilized inorganic compound onto a substrate, a process known as vapor-depositing or alternatively, vapor grafting. Preferably the deposition occurs on one of a plurality of chemically active sites located on the substrate. In one embodiment, the active sites are positioned on a surface of the substrate. In a preferred set of embodiments, the substrate is a porous material, "porous material" being defined as having a plurality of inner channels and pores penetrating the substrate. Thus in a porous material, the chemically active sites can be positioned on a surface of the channels and pores. The deposited inorganic compound may be a transient intermediate or may be stable at 25° C. When the chemically active sites comprise oxygen functionalities such as a hydroxyl or an epoxy group, the inorganic compound may be attached to the substrate by a covalent bond to the oxygen functionality. The bonding may occur between the oxygen functionality and the metal center.

It is a feature of the techniques of the invention that particularly strong covalent-type bonding occurs between the inorganic compound and the porous substrate. This is reflected in the fact that the inorganic compound bonds to the porous substrate to the extent that it is immobilized at the substrate under sublimation conditions. "Sublimation conditions", in this context, means conditions in which the inorganic compound, non-covalently attached to a surface, would sublime. It is another feature that the bond strength is sufficient to immobilize the inorganic compound at the substrate under reflux conditions in a solvent in which the inorganic compound is soluble. This strong bonding is reflected in one molecular structure representation that can be achieved according to techniques of the invention defining SUBSTRATE—O—M—L. The bond between O and M is a covalent bond.

A feature of one deposition method of the invention is the production of monolayered materials in some cases. With prior art deposition methods, a deposited first layer can act as a substrate for deposition of a second layer which in turn acts as a substrate for a third layer. In a preferred embodiment, the deposition involves a chemical reaction between the inorganic complex and a chemically active site having a desired chemical functionality. Once the inorganic complex or metal compound occupies the site, deposition cannot occur on that site or on the inorganic complex or metal compound. If the resulting material is to be used for catalytic applications, the methods of the present invention has a benefit over prior art layered materials in that a deposited catalyst can be disperse and isolated.

It is advantageous to deposit the metal compound within pores of a porous material, especially for catalytic applications. When catalysis occurs inside pores, the reaction is isolated and selectivity is enhanced. When an organic reactant is particularly large and/or sterically demanding, high surface areas are necessary to achieve high catalytic activity. In one embodiment, the pores of the porous material are designed to have a pore size to allow the entry and exit of species having molecular dimensions. The porous material preferably has a pore size of at least about 8 Å, more preferably at least about 10 Å, more preferably at least 20 Å, more preferably still at least about 25 Å, more preferably still at least about 30 Å, more preferably still at least about 40 Å, more preferably still at least about 50 Å, more preferably still at least about 60 Å, more preferably still at least about 70 Å, more preferably still at least about 80 Å, more preferably still at least about 90 Å and more preferably still at least about 100 Å. In one preferred embodiment the porous material has a pore size of from about 10 to 50 Å, more preferably from about 20 to about 40 Å, and more preferably still from about 25 to about 35 Å.

In another embodiment, the porous material has a porosity volume of at least about 5%. "Porosity volume" as used herein is defined as a total volume of the pores and channels. The volume is designed to allow the entry and exit of species having molecular dimensions. Preferably the porosity volume is at least about 10%, more preferably at least about 15%, more preferably still at least about 20%, more preferably at least about 30%, more preferably still at least about 40%, more preferably still at least about 50%, more preferably still at least about 60%, and more preferably still at least about 70%.

In yet another embodiment the pores and channels of the porous material provides a surface area of at least 10 $m^2/g$ wherein the surface area is defined as a total area of the internal and external surfaces of the material. "Internal surface" as used herein is defined as a surface of a pore or channel and "external surface" as used herein is defined as a surface on the outside of the article or alternatively a surface that does not comprise a pore or a channel. Preferably the surface area is at least about 20 $m^2/g$, more preferably at least about 30 $m^2/g$, more preferably still at least about 40 m²/g, more preferably still at least about 50 m²/g, more preferably still at least about 60 m²/g, more preferably still at least about 70 m²/g, more preferably still at least about 80 m²/g, more preferably still at least about 90 m²/g, and more preferably still at least about 100 m²/g.

The metal compound that is eventually deposited on the substrate can be selected from the group consisting of a metal, a metal alloy, a metalloid, a metal complex, a metalloid complex and any combination thereof. The metal compound is highly disperse and can be deposited on either the internal or external surfaces of the substrate. Where a material comprises the deposited metal compound on the substrate, the material, according to one set of embodiments, loses surface area of no more than about 90%, more preferably no more than about 75%, more preferably no more than about 50%, preferably no more than about 35%, more preferably still less than about 20%, and more preferably still less than about 10%. Preferably the deposited material has a surface area of at least about 20 m²/g, more preferably at least about 30 m²/g, more preferably still at least about 40 m²/g, more preferably still at least about 50 m²/g, more preferably still at least about 60 m²/g, more preferably still at least about 70 m²/g, more preferably still at least about 80 m²/g, more preferably still at least about 90 m²/g, and more preferably still at least about 100 m²/g. The resultant, deposited material, in one set of embodiments, has an atomic or molecular size of less than about 5 Å, more preferably less than about 10 Å, more preferably still less than about 15 Å.

In a preferred set of embodiments the technique results in a porous material in which at least about 50% of the original pores remain unblocked. That is, the continuous pathways that define the original porous structure remain open in an amount of at least 50%, following chemical vapor deposition. Preferably, at least about 60%, more preferably still at least about 70%, more preferably still at least about 80%, more preferably still at least about 90%, and more preferably still at least about 95% of the original pores of the porous structure remain unblocked after chemical vapor deposition.

Preferably the metal compound including metals or metalloid atoms, complexes or mixtures have atomic, molecular, or complex sizes of less than about 5 Å, preferably less than about 10 Å, more preferably less than about 15 Å, more preferably less than about 20 Å, more preferably still at less than about 30 Å, more preferably less than about 40 Å, and more preferably still less than about 50 Å, on average. In one set of preferred embodiments the metal or metalloid atoms, complexes or mixtures have atomic, molecular, or complex size of between about 10 and about 50 Å, more preferably from about 20 to about 40 Å, more preferably still from about 25 to about 35 Å.

In one embodiment the porous material is MCM-41 (as described in U.S. Pat. Nos. 5,057,296, 5,098,684, and 5,102,643, incorporated herein by reference). In another embodiment the porous material is a structure as defined in co-pending, commonly-owned U.S. patent application Ser. No. 08/734,170, filed Oct. 21, 1996 by Ying, et al., entitled "Metalloporphyrin Oxidation Catalyst Covalently Coupled to an Inorganic Surface and Method of Making Same", incorporated herein by reference.

In another embodiment the material, comprising a deposited metal compound on a substrate, is a catalyst. Preferably the catalyst is stable at high temperatures such that the stability allows the catalyst to be used for a wide variety of catalytic reactions.

Preferably the catalyst is stable to a temperature of at least about 75° C., more preferably at least 100° C., more preferably still at least about 125° C., and more preferably still at least about 150° C. In another set of embodiments, where the deposited material is a metal oxide, these levels of preferred maximum decomposition occur at a temperature of at least about 300° C., more preferably still at least about 400° C., more preferably still at least about 500° C., and more preferably still at least about 600° C.

In another embodiment, deposition of the metal compound results in the deposition of a film on a surface of the substrate. The film can be continuous or discontinuous, that is, each atom, molecule, or complex defining the film can be in physical contact with at least one other, similar species resulting in complete coverage of the porous substrate, or can be discontinuous in which exposed portions of the substrate remain. The metal film can have a surface area of at least about 25 m²/g, 50 m²/g, 75 m²/g, 100 m²/g, 125 m²/g, 175 m²/g, or, in a particularly preferred embodiment, at least about 200 m²/g.

In another embodiment, the method involves depositing a metal compound by using techniques analogous to chemical vapor deposition (CVD), CVD techniques being well known in the art. Chemical vapor deposition can be carried out with flow of an inert carrier gas at or near atmospheric pressure using compounds having a sublimation point of from about 80 to about 160° C., more preferably from about 100 to about 150° C., which compounds decompose at higher temperatures.

In another embodiment chemical vapor deposition can be carried out under vacuum in which, downstream from the porous substrate the surface of which is coated via chemical vapor deposition is a low-temperature trap, and this embodiment typically is used in connection with compounds having a sublimation point of at least about 150° C., or about 170° C., or at least about 200° C., which compounds are unstable under sublimation conditions to the extent that unacceptable degradation and decomposition occurs, under conditions at or near atmospheric pressure.

As mentioned previously, deposition of a metal compound can result in complete coverage of a surface of the substrate with the deposited compound onto a plurality of active sites. Another aspect of the present invention provides a method to control the amount of coverage by pretreating the surface. A benefit of this method is a control of a number of chemically active sites for deposition. Pretreatment methods of this invention can result in a uniformly disperse or dilute number of active sites. In one embodiment, pretreatment involves modifying a chemical functionality of an active site. Thus, pretreatment of a substrate having a plurality of chemically active sites of a first chemical functionality results in a substrate having a plurality of chemically active sites of a second chemical functionality. In another embodiment, 1–25% of the sites retain the first chemical functionality after pretreatment and 99–75% of the sites have a second functionality. In another embodiment, pretreatment provides a surface where deposition of a metal compound occurs on a site having the first chemical functionality whereas the second chemical functionality prevents deposition of the metal compound. A preferred pretreatment method involves providing a surface of a substrate having a plurality of hydroxyl functionalities and exposing this surface to a compound having a formula $R_3SiX$. R can be selected from the group consisting of $C_1$–$C_{10}$ alkyl, and aryl and X can be selected from the group consisting of halide and $C_1$–$C_6$ alkoxide. In another embodiment, the surface containing hydroxyl functionalities is pretreated with $R_3SiCl$, to provide a surface having 1–25% of the plurality of sites with hydroxyl functionalities and 99–75% of the plurality of sites with silyloxide ($OSiR_3$) functionalities.

FIG. 1 depicts a schematic showing pretreatment of a surface with $R_3SiX$. Referring to FIG. 1, the surface has a plurality of hydroxyl groups. The addition of $R_3SiX$ results in the removal of the hydroxyl groups by forming O—Si bonds accompanied by the elimination of HX. Deposition of a metal compound only occurs on any remaining hydroxyl terminated sites and cannot occur on silyloxide-terminated sites. Because the number of sites for deposition is reduced, deposition of on this pre-treated surface results in a uniformly dispersed metal compound on the surface.

In another embodiment, the pretreatment step involves heating the surface to a temperature of less than about 600° C. and subjecting the surface to a vacuum of $10^{-2}$ torr. The pretreatment step provides metal loading of about 10–30 wt % metal, preferably about 20–25 wt % of metal. At a temperature of less than about 150° C. and a vacuum of $10^{-2}$ torr, metal loadings of about 10–25 wt % can be achieved, preferably between about 15–20 wt %.

Another aspect of the invention provides the use of a deposited metal compound on a substrate as a heterogeneous catalyst. In catalysis, the catalyst transforms a reactant into a product. The reactant is soluble or at least partially soluble in an organic solvent or in water. When the catalyst is a "homogenous catalyst" the catalyst is at least partially soluble in the organic solvent in water. When the catalyst is a "heterogenous catalyst" the catalyst is insoluble in the organic solvent or water. Traditional heterogeneous catalyst include solids such as metal and metal oxides. Advantages of heterogeneous catalysts include stability in air and/or water and upon completion of the catalytic reaction, heterogenous catalysts are easily recoverable. The disadvantages of some heterogeneous catalysts include lack of selectivity.

It is a feature of the present invention to provide a new type of heterogeneous catalyst that shows improved selectivity and activity over prior art heterogeneous catalysts while maintaining the advantages of heterogeneous catalysts. In one embodiment, the substrate is a porous metal substrate, to provide a heterogeneous catalyst with a higher surface area over prior art heterogeneous catalysts, including metal particles or metal colloid particles. A "metal colloid" is defined herein as metal particles suspended in a medium. Because of the high surface area of the catalyst in the present invention, preferred embodiments involve depositing metal compounds that are highly and uniformly dispersed within the material.

In another embodiment, the materials of the present invention catalyze carbon-heteroatom coupling reactions between a reactive carbon atom and a reactive heteroatom. The coupling reactions can be intramolecular, that is, both the reactive carbon and heteroatom are positioned on one molecule. The coupling reactions can be intermolecular where the reactive carbon is situated on a first molecule and the reactive heteroatom is positioned on a second molecule. The heteroatom can be selected from the group consisting of carbon and nitrogen.

Typically, prior art homogeneous and heterogeneous carbon-heteroatom coupling reactions must be performed under an inert atmosphere such as argon. It is a feature of the present invention that a carbon-heteroatom coupling reaction can be carried out in air, wherein at least about 5% conversion is achieved within about 1 h.

In another embodiment, the catalyst of the present invention catalyzes carbon-carbon coupling reactions. Preferably the carbon-carbon coupling occurs between two unsaturated carbon atoms, wherein an unsaturated carbon atom is defined as a carbon that is involved in p-π bonding. In a preferred embodiment, the carbon-carbon coupling reaction is a Heck reaction. The Heck reaction can occur between a wide range of functional groups on both coupling partners which gives the Heck reaction a versatility that provides a powerful tool in organic synthesis. Several homogeneous catalyst are available to catalyze the Heck reaction. The present invention provides a heterogeneous catalyst for the Heck reaction that shows comparable activity and selectivity to homogeneous catalysts. Moreover, the catalysts of the present invention can be easily recovered.

The articles, compositions, and methods of the invention can be used in catalytic coupling reactions, homogeneous catalysis, heterogeneous reactions such as hydrogenation, partial oxidation, and the like. Each of the above-described preferred composition parameters, be they physical, structural, or chemical, or method parameters including methods of making and use can be used in combination with any others of these parameters at any level of those described as preferred, in preferred embodiments.

Figure 2:
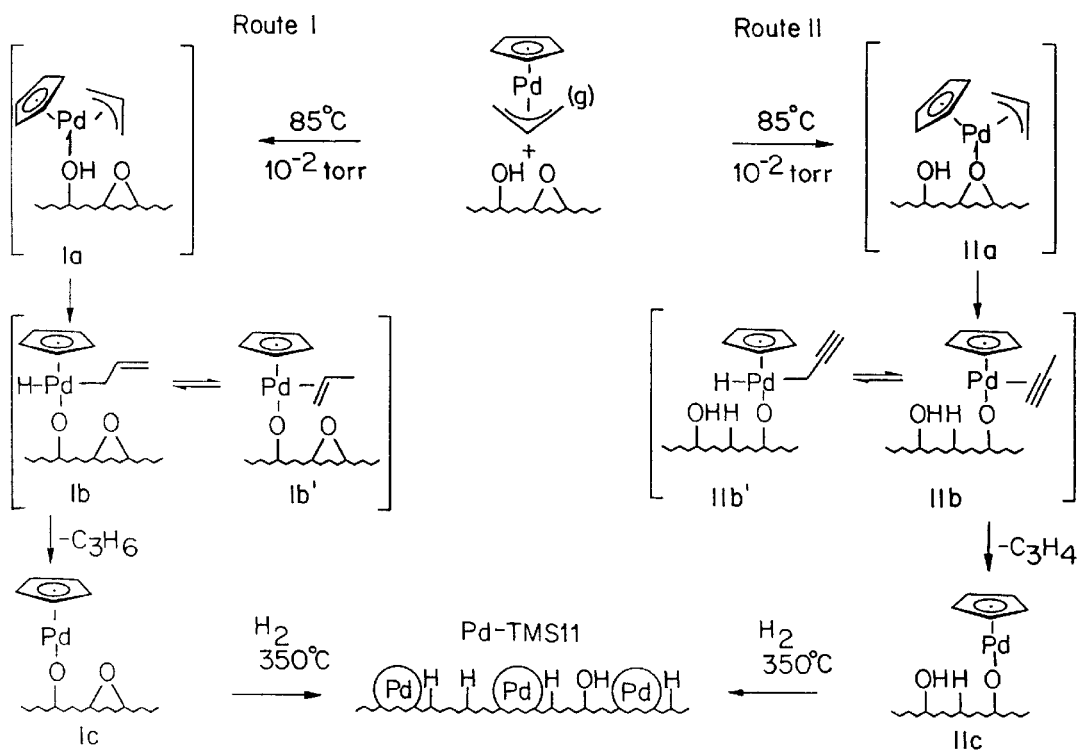
FIG. 2 shows a schematic of a proposed mechanism for deposition palladium metal on a surface.

Another embodiment of the invention provides a heterogeneous catalyst comprising a metal deposited on a pretreated surface of a porous material. The metal may be selected from the group consisting of alkaline metals, alkaline earth metals, transition metals, lanthanides and actinides. In a preferred embodiment, the metal is palladium. FIG. 2 shows a schematic of a proposed mechanism for deposition palladium metal on a surface. FIG. 2 is included for illustrative purposes and it is not intended to limit the invention to the mechanism described herein. Referring to FIG. 2, the palladium metal is provided by a palladium cyclopentadiene allyl complex. The palladium complex reacts with a hydroxyl group to result in a palladium hydroxyl intermediate. An allyl group also situated on the palladium can react with a hydroxyl proton. Elimination of propene follows to yield a palladium oxide compound. Subjecting the catalyst to hydrogenation at high temperatures produces palladium deposited on the surface. Alternative mechanisms includes deposition of the palladium complex onto an epoxy group in which a palladium oxide intermediate is subjected to a reaction with the hydroxyl proton. An elimination product can be propyne and hydrogenation of the palladium oxide complex produces the palladium metal deposited on the surface. It has been proposed that a palladium (0) compound is the reactive species in a Heck reaction.

In the above and other embodiments the deposited material can be a catalyst.

According to another aspect, the invention provides a series of products.

The metal, metalloid, or complex of either can be a combination of any, and can include metal oxides, metal sulfides, and the like.

The porous substrate can have a pore volume of at least 10%, or other levels described above.

The porous substrate can have a pore size of at least about 5 Å, more preferably at least about 10 Å, more preferably at least about 15 Å, more preferably at least about 25 Å, more preferably at least about 35 Å, more preferably at least about 55 Å, more preferably at least about 75 Å, or in one set of embodiments, has a pore size up to about 100 Å, on average.

Preferably, degradation in an amount less than about 50% takes place and/or the degradation takes places over a period of time of at least 2 hours.

Preferably, the heterogeneous catalysis has a selectivity of at least about 80%, more preferably at least about 90%, more preferably still at least about 95%.

The surface-immobilized catalyst is palladium, a palladium complex, or a mixture according to preferred embodiments. In a particularly preferred embodiment, the catalyst is palladium.

In preferred embodiments the surface-immobilized catalyst has a surface area of at least about 10 $m^2/g$, more preferably a surface area according to the above-described preferred surface area minimum levels.

The function and advantage of these and other embodiments of the present invention will be more fully understood from the examples below. The following examples are intended to illustrate the benefits of the present invention, but do not exemplify the full scope of the invention.

EXAMPLE 1

Modified Synthesis of MCM41

Materials. The following chemicals were obtained from Strem Chemical and used without any further purification: Molybdenum carbonyl, bis(cyclopentadienyl)chromium, cobalt(II) acetylacetonate [Co(acac)$_2$], bis(cyclopentadienyl)nickel, tetrakis(diethylamino)zirconium, tetrakis(dimethylamino)titanium, tris(2,2,6,6-tetramethyl-3,5-heptanedionato)scandium/yttrium [M(TMHD)$_3$] (M=Sc, Y), tris(cyclopentadienyl)-lanthanum, pentamethylcyclopentadienylrhenium tricarbonyl, palladium(II) chloride. Hexadecyl-trimethylammonium bromide was supplied by Alfa Chemicals. Dodecane, N,N-dimethylacetamide, chlorobenzene, bromobenzene, 1-bromo-4-nitrobenzene, 4-bromoacetophenone, triethylamine, butyl acrylate, sodium silicate (14% NaOH/27% SiO$_2$), silica gel (grade 62), magnesium sulfate and Celite were obtained from Aldrich Chemical Company. Allylpalladium cyclopentadienyl was prepared according to a literature procedure by the reaction of allylpalladium chloride dimer (Strem) and cyclopentadienylmagnesium chloride (Aldrich). Palladium on aluminium oxide (10%) and on carbon (10%) was supplied by Aldrich Chemical Company.

Instrumentation. The X-ray powder diffraction data were recorded on a Siemens D5000 diffractometer using nickel-filtered Cu$_{K\alpha}$. Transmission electron micrographs were taken on a JEOL 200CX transmission electron microscope equipped with a lanthanum hexaboride (LaB$_6$) gun operating at an accelerating voltage of 200 kV and with an objective aperture of 60 mm. TEM samples were ground, sonicated in isopropanol, and supported on a carbon-coated copper grid. Nitrogen adsorption isotherms were taken at 77 K on a Micromeritics ASAP 2010 Gas Sorption and Porosimetry System. Samples were normally prepared for measurement by degassing at 150° C. under vacuum until a final pressure of $1 \times 10^{-3}$ torr was reached. B.E.T. (Brunauer-Emmett-Teller) surface areas were determined over a relative pressure range from 0.005 to 0.20 (Gregg and Sing, 1982). Mesopore size distributions were calculated using the B.J.H. (Brunauer-Joyner-Halenda) method off the adsorption branch of the isotherms.

Hexadecyltrimethylammonium bromide (15.9 g, 44.9 mmol) was dissolved in H$_2$O (1.2 L) and treated with sodium silicate (14% NaOH/27% SiO$_2$) in H$_2$O(0.4 L) to produce a white precipitate. The pH value of the mixture was adjusted to pH=11.5 using sulfuric acid (30%). The gel was aged at room temperature for 12 h before it was heated in pressure tubes to 100° C. for 7 days. The supernatant of the aged gel was decanted off and the resulting white residue washed with H$_2$O(1 L) and EtOH (1 L). The isolated solid was dried in air at room temperature for 12 h before the material was calcined at 560° C. for 6 h giving MCM-41.

EXAMPLE 2

Palladium Grafted MCM-41 (Pd-TMS 11/11)

MCM-41 (0.5 g) (XRD (100) 39.9 Å, B.E.T. surface area of 997 $m^2/g$, BJH adsorption pore size of 27.4 Å) was degassed at 600° C. under reduced pressure ($10^{-2}$ torr) for 6 h. The resulting material was loaded into a short path frit and contained with glass wool under an inert gas atmosphere. A small round-bottom flask was filled with the red complex [Pd(h$^3$-C$_3$H$_5$)(h—C$_5$H$_5$)] (0.25 g, 1.2 mmol) and connected to a prepared frit that was further attached to a condensation bridge with a round bottom flask. The apparatus was evacuated, and a constant pressure ($10^{-2}$ torr) was maintained by cooling the empty round-bottom flask to −196° C. The small round-bottom flask containing the volatile palladium complex and the loaded frit were heated to 120° C. (ramp 1° C./min) using an oil bath. During the heating process, the white MCM-41 staring material turned black and the excess volatile organometallic complex was condensed into the cooled round-bottom flask. The resulting solid was reduced under a stream of hydrogen (50 mL/min) at 350° C., giving a black powder designated Pd-TMS11. The XRD spectrum showed a (100) peak at 39.6 Å, distinct (110) and (200) peaks, and analysis of the surface area by the B.E.T. method gave 753 $m^2/g$ with a BJH adsorption pore size of 26.5 Å. Carbon monoxide adsorption analysis found a metal dispersion of 26.1% and a metallic surface area of 116 $m^2/g$ (Pd metal). Elemental analysis of the metal content gave 19.1% Pd by weight.

EXAMPLE 3

Palladium Grafted MCM-41 (Pd-TMS11/2)

The preparation of Pd-TMS11/2 was carried out identically to Pd-TMS1, with the exception of a higher concentration of the volatile palladium complex. Degassed MCM-41 (0.3 g) was treated with [Pd(h$^3$—C$_3$H$_5$)(h—C$_5$H$_5$)] (0.2 g, 0.9 mmol) and further work-up procedures resulted in the isolation of a black powder, designated Pd-TMS11/2. The XRD spectrum showed a (100) peak at 39.6 Å, distinct (110) and (200) peaks, and analysis of the surface area by the B.E.T. method gave 715 $m^2/g$ with a BJH adsorption pore size of 26.5 Å. Carbon monoxide adsorption analysis found a metal dispersion of 31.1% and a metallic surface area of 139 $m^2/g$ (Pd metal). Elemental analysis of the metal content gave 22.3% Pd by weight.

EXAMPLE 4

Palladium Grafted MCM-41 (Pd-TMS11/3)

The preparation of Pd-TMS11/3 was carried out identically to the preparation of Pd-TMS11, with the exception of the use of a silane treated MCM-41 material and a lower concentration of the volatile palladium complex. MCM-41 (1.8 g) (XRD (100) 38.4 Å, (200) 19.2 Å, (210) 14.6 Å; BET surface area of 1004 $m^2/g$, BJH adsorption pore size of 23.9 Å) was degassed at 150° C. under reduced pressure ($10^{-2}$ torr) for 6 h before it was treated with chlorotrimethylsilane (5.56 g, 79 mmol) in n-heptane (100 mL). After the mixture was refluxed for 5 h the supernatant was filtered off and the resulting solid washed with pentane (3×100 mL). To ensure that the silanized support material was free of all solvent and silane residues the material was dried under reduced pressure ($10^{-2}$ torr) at room temperature for 12 h giving a white powder (XRD (100) 38.4 Å, (110) 22.1 Å, (200) 19.2 Å, (210) 14.6 Å; BET surface area of 824 $m^2/g$, BJH adsorption pore size of 21.4 Å; FT-IR; ν(C—H) 2966 s, 2910 m cm$^{-1}$; $^{13}$C—CP/MASS NMR: δ–1.1 [—Si(CH$_3$)$_3$] ppm; $^{29}$Si—CP/MASS NMR: δ–111.0, –106.9 [Si—O—Si], 14.4 [—Si(CH$_3$)$_3$] ppm; Elemental Analysis (wt %): C, 6.4; H, 1.3, N, <0.05%. The pretreated MCM-41 material (0.3 g) was treated with [Pd(η$^3$—C$_3$H$_5$) (η—C$_5$H$_5$) (0.05 g, 0.23 mmol) following the vapor grafting preparation described for Pd-TMS11 giving palladium grafted mesoporotis material with a significant reduced metal content. The XRD spectrum showed a (100) peak at 38.4 Å, distinct (110) and (200) peaks, and analysis of the surface area by the BET method gave 632 m$^2$/g with a BJH adsorption pore size of 21.1 Å. Elemental analysis of the metal content gave 1.6% Pd by weight.

For the scale-up of the vapor depositing process a fluidized bed reactor (FIG. 3) has been utilized. In a typical run the porous support material was kept in a stream of inert gas which was saturated with the volatile grating agent. For the large scale preparation of Pd-TMS11/3, silanized MCM-41 material (15 g) and [Pd(η$^3$—C$_3$H$_5$) (η—C$_5$H$_5$) (0.05 g, 0.23 mmol) were loaded into the large scale vapor grafting reactor under inert gas atmosphere. The porous support material and the volatile palladium complex were kept separated via a porous frit. The outside of the reactor was warmed to 120° C. (ramp 1° C./min) for 2 h using a heating tape and a continuous flow of argon was applied to generate a fluidized bed of the support material. The resulting material was reduced under a stream of hydrogen at 350° C. for 3 h giving Pd-TMS11/3.

EXAMPLE 5

Molybdenum Carbonyl Grafted MCM-41 (Mo(CO)-TMS 11)

MCM-41 (0.5 g) (XRD (100) 34.9 Å, B.E.T. surface area of 640 m$^2$/g, BJH adsorption pore size of 32.9 Å) was heated in a tubular reactor under a stream of argon (100 mL/min) at 300° C. After a period of 3 h, the degassed sample was brought to room temperature and the reactor loaded with Mo(CO)$_6$ (300 mg, 1.14 mmol) under an inert gas atmosphere. Heating of the charged reactor to 50° C. under a stream of argon (100 mL/min) for 3 h afforded a gray-white powder, designated Mo(CO)-TMS11. The resulting air stable material was thermally sensitive and decomposed if heated above 120° C. with the loss of the carbonyl ligand. The IR spectrum of the material exhibited a strong absorption in the carbonyl region at n(CO)=1969 cm$^{-1}$. The XRD spectrum of the material showed a (100) peak centered at 34.5 Å, and a B.E.T. surface area analysis gave 473 m$^2$/g. Elemental analysis gave 0.85% C; 0.4% H; <0.05% N; and 3.8% Mo by weight.

EXAMPLE 6

Molybdenum Grafted MCM41 (Mo-TMS11)

MCM-41 (0.5 g) (XRD (100) 34.9 Å, B.E.T. surface area of 640 m$^2$/g, BJH adsorption pore size of 32.9 Å) was heated in a tubular reactor under a stream of argon (100 mL/min) at 300° C. After a period of 3 h, the degassed sample was brought to room temperature and the reactor loaded with Mo(CO)$_6$ (300 mg, 1.14 mmol) under an inert gas atmosphere. Heating of the charged reactor to 50° C. under a stream of argon (100 mL/min) for 3 h and subsequent heating to 200° C. (ramp 1° C./min) resulted in the formation of a gray-black powder, designated Mo-TMS11. The recorded XRD spectrum showed a (100) peak at 36 Å, weak (110) and (200) peaks, and a B.E.T. surface area of 554 m$^2$/g with a BJH adsorption pore size of 30.6 Å. Elemental analysis established 0.9% C; 0.4% H; <0.05% N; and 2.1% Mo by weight.

EXAMPLE 7

Molybdenum Sulfide Grafted MCM-41 (MoS-TMS11)

MCM-41 (0.5 g) (XRD (100) 34.9 Å, B.E.T. surface area of 640 m$^2$/g, BJH adsorption pore size of 32.9 Å) was heated in a tubular reactor under a stream of argon (100 mL/min) at 300° C. After a period of 3 h the degassed sample was brought to room temperature and the reactor loaded with Mo(CO)$_6$ (300 mg, 1.14 mmol) under an inert gas atmosphere. After the reactor was heated to 50° C. under a stream of argon (100 mL/min) for 3 h, the temperature was raised to 200° C. (ramp 1° C./min). The resulting powder was cooled to room temperature and then heated under a stream of H$_2$S (50 mL/min) to 200° C. for 3 h giving a black material, designated MoS-TMS11. The XRD spectrum showed a (100) peak at 33.5 Å, weak (110) and (200) peaks, and a B.E.T. surface area of 193 m$^2$/g. Elemental analysis established 1.8% C; 0.6% H; <0.05% N; 2.2% Mo; and 2.9% S by weight.

EXAMPLE 8

Chromium Oxide Grafted MCM-41 (CrO-TMS11)

MCM-41 (0.3 g) (XRD (100) 39.9 Å, B.E.T. surface area of 997 m$^2$/g, BJH adsorption pore size of 27.4 Å, 1.5% Nb by weight dopant) was degassed at 600° C. under reduced pressure (10$^{-2}$ torr) for 6 h. The resulting material was loaded into a short path frit and contained with glass wool under an inert gas atmosphere. A small round-bottom flask was filled with [Cr(h—C$_5$H$_5$)$_2$] (0.3 g, 1.37 mmol) and connected to the prepared frit that was further attached to a condensation bridge with a round bottom flask. The apparatus was evacuated, and a constant pressure (10$^{-2}$ torr) was maintained by cooling the empty round-bottom flask to –196° C. The small round bottom flask containing the organometallic complex and the loaded frit was heated to 100° C. (ramp 1° C./min) using an oil bath. During the heating process, the white MCM-41 staring material turned dark gray and the excess volatile organometallic complex was condensed into the cooled round-bottom flask. The resulting solid was exposed to air and further calcination at 600° C. for 6 h gave a green powder, designated CrO-TMS11. The XRD spectrum showed a (100) peak at 39.9 Å and distinct (110) and (200) peaks, and analysis of the surface area by the B.E.T. method gave 731 m$^2$/g with a BJH adsorption pore size of 27.1 Å. Elemental analysis gave 0.15% C; 0.1% H; <0.5% N; and 4.5% Cr by weight.

EXAMPLE 9

Cobalt Oxide Grafted MCM-41 (CoO-TMS11)

MCM-41 (1.0 g) (XRD (100) 35.5 Å, B.E.T. surface area of 844 m$^2$/g, BJH adsorption pore size of 25.9 Å) was loaded together with [Co(acac)$_2$] (1.0 g, 3.9 mmol) in a pyrolysis tube in which the solids were separated by a 10 cm glass wool layer. The reaction vessel was placed in a tube furnace and it was ensured that the volatile cobalt complex and the MCM-41 material were fully exposed to the heat process. After heating the materials at 300° C. for 5 h under reduced pressure (10$^{-2}$ torr), a green solid was isolated. Calcination of the resulting material at 600° C. for 5 h in air gave a blue powder, designated CoO-TMS11. The recorded XRD spectrum showed a (100) peak at 35.1 Å and distinct (110) and (200) peaks, and analysis of the surface area by the B.E.T. method gave 568 m$^2$/g with a BJH adsorption pore size of 25.9 Å. Elemental analysis of the metal content gave 14.7% Co by weight.

EXAMPLE 10

Nickel Grafted MCM-41 (Ni-TMS11)

MCM-41 (0.5 g) (XRD (100) 39.9 Å, B.E.T. surface area of 997 m$^2$/g, BJH adsorption pore size of 27.4 Å, 1.5% Nb by weight dopant) was degassed at 600° C. under reduced pressure (10$^{-2}$ torr) for 6 h. The resulting material was loaded into a short path frit and contained with glass wool under an inert gas atmosphere. A small round-bottom flask was filled with [Ni(h—C$_5$H$_5$)$_2$] (0.35 g, 1.85 mmol) and connected to the prepared frit that was further attached to a condensation bridge with a round bottom flask. The apparatus was evacuated, and a constant pressure (10$^{-2}$ torr) was maintained by cooling the empty round-bottom flask to —196° C. The small round bottom flask containing the organometallic complex and the loaded frit was heated to 85° C. (ramp 1° C./min) using an oil bath. During the heating process, the white MCM-41 staring material turned dark beige and the excess volatile organometallic complex was condensed into the cooled round bottom flask. The resulting solid was reduced under a stream of hydrogen at 300° C. for 3 h, giving a black powder designated Ni-TMS11. The XRD spectrum showed a (100) peak at 37.2 Å and distinct (110) and (200) peaks, and analysis of the surface area by the B.E.T. method gave 793 m$^2$/g with a BJH adsorption pore size of 26.7 Å. Elemental analysis gave <0.1% C; <0.1% H; <0.05% N; and 7.1% Ni by weight.

EXAMPLE 11

Zirconium Oxide Grafted MCM-41 (ZrO-TMS11)

MCM-41 (0.5 g) (XRD (100) 35.5 Å, B.E.T. surface area of 845 m$^2$/g, BJH adsorption pore size of 25.9 Å) was degassed at 600° C. under reduced pressure (10$^{-2}$ torr) for 6 h. The resulting material was loaded into a short path frit and contained with glass wool under an inert gas atmosphere. A small round-bottom flask was filled with [Zr{N(CH$_2$CH$_3$)$_2$}$_4$] (2.0 g, 5.3 mmol) and was connected to the prepared frit that was further attached to a condensation bridge with a round-bottom flask. The apparatus was evacuated and a constant pressure (10$^2$ torr) was maintained by cooling the empty round bottom flask to −196° C. The small round-bottom flask containing the volatile zirconium complex and the loaded frit were heated to 140° C. (ramp 1° C./min) using an oil bath. During the heating process, the white MCM-41 staring material turned pink and the excess volatile organometallic complex was condensed into the cooled round-bottom flask. The resulting solid was calcined in air at 600° C. for 6 h, giving a white powder designated ZrO-TMS11. The XRD spectrum showed a (100) peak at 34.0 Å, and analysis of the surface area by the B.E.T. method gave 579 m$^2$/g with a BJH adsorption pore size of 26.7 Å. Elemental analysis of the metal content gave 2.3% Zr by weight.

EXAMPLE 12

Scandium Oxide Grafted MCM-41 (ScO-TMS11)

MCM-41 (1.0 g) (XRD (100) 40.9 Å, B.E.T. surface area of 1041 m$^2$/g, BJH adsorption pore size of 24.3 Å) was loaded together with [Sc(TMHD)$_3$] (0.5 g, 0.8 mmol) in a pyrolysis tube in which the solids were separated by a 10 cm glass wool layer. The reaction vessel was placed in a tube furnace and it was ensured that the volatile scandium complex and the MCM-41 material were fully exposed to the heat process. After heating the materials at 150° C. (ramp 0.5° C./min) for 10 h under reduced pressure (10$^2$ torr) a pink solid was isolated. Calcination of the resulting material at 600° C. for 24 h in air gave a white powder, designated ScO-TMS11. The XRD spectrum showed a (100) peak at 38.0 Å, distinct (110) and (200) peaks, and analysis of the surface area by the B.E.T. method gave 977 m$^2$/g with a BJH adsorption pore size of 24.1. A Elemental analysis gave 0.1% C; 0.1% H; <0.05% N; and 2.1% Sc by weight.

EXAMPLE 13

Yttrium Oxide Grafted MCM-41 (YO-TMS11)

MCM-41 (0.3 g) (XRD (100) 40.9 Å, B.E.T. surface area of 1041 m$^2$/g, BJH adsorption pore size of 24.3 Å) was loaded together with [Y(TMHD)$_3$] (0.35 g, 0.6 mmol) in a pyrolysis tube in which the solids were separated by a 10 cm glass wool layer. The reaction vessel was placed in a tube furnace and it was ensured that the volatile yttrium complex and the MCM-41 material were fully exposed to the heat process. After heating the materials at 150° C. (ramp 0.5° C./min) for 10 h under reduced pressure (10$^2$ torr) a pink solid was isolated. Calcination of the resulting material at 600° C. for 12 h in air gave a white powder, designated YO-TMS11. The XRD spectrum showed a (100) peak at 39.7 Å, distinct (110) and (200) peaks, and analysis of the surface area by the B.E.T. method gave 890 m$^2$/g with a BJH adsorption pore size of 23.5 Å. Elemental analysis gave <0.1% C; <0.1% H; <0.05% N; and 1.9% Y by weight.

EXAMPLE 14

Lanthanum Oxide Grafted MCM-41 (LaO-TMS11)

MCM-41 (0.3 g) (XRD (100) 35.5 Å, B.E.T. surface area of 845 m$^2$/g, BJH adsorption pore size of 25.9 Å) was degassed at 600° C. under reduced pressure (10$^{-2}$ torr) for 6 h. The degassed material was loaded together with [La(h—C$_5$H$_5$)$_3$] (1.0 g, 3.0 mmol) in a pyrolysis tube in which the solids were separated by a 10 cm glass wool layer. The reaction vessel was placed in a tube furnace and it was ensured that the volatile lanthanum complex and the MCM-41 material were fully exposed to the heat process. After heating the materials at 350 ° C. (ramp 2.0° C./min) for 3 h under reduced pressure (10$^{-2}$ torr) a yellow solid was isolated. Calcination of the resulting material at 540° C. for 6 h in air gave a white powder, designated LaO-TMS11. The XRD spectrum showed a (100) peak at 32.8 Å, distincet (110) and (200) peaks, and analysis of the surface area by the B.E.T. method gave 433 m$^2$/g. Elemental analysis gave 0.1% C; 0.5% H; <0.05% N; and 8.7% La by weight.

EXAMPLE 15

Rhenium Oxide Grafted MCM-41 (ReO-TMS11)

MCM-41 (0.5 g) (XRD (100) 39.9 Å, B.E.T. surface area of 997 m$^2$/g, BJH adsorption pore size of 27.4 Å, 1.5% Nb by weight dopant) was degassed at 600° C. under reduced pressure (10$^{-2}$ torr) for 6 h. The degassed material was loaded together with [Re {h—C(CH$_3$)$_5$}(CO)$_3$] (0.25 g, 0.6 mmol) in a pyrolysis tube in which the solids were separated by a 10 cm glass wool layer. The reaction vessel was placed in a tube furnace and it was ensured that the volatile rhenium complex and the MCM-41 material were fully exposed to the heat process. After heating the materials at 150° C. (ramp 1.0° C./min) for 3 h under reduced pressure (10$^{-2}$ torr), a gray solid was isolated. The resulting material exhibited IR-active n(CO) absorption at 2013 and 1911 cm$^{-1}$. Calcination of the material at 500° C. for 3 h in air gave a white powder, designated ReO-TMS11. The XRD spectrum showed a (100) peak at 38.9 Å, distinct (110) and (200) peaks, and analysis of the surface area by the B.E.T. method gave 793 m$^2$/g with a BJH adsorption pore size of 26.1 Å. Elemental analysis gave 1.0% C; <0.1% H; <0.05% N; and 6.9% Re by weight.

EXAMPLE 16

Rhenium Grafted MCM-41 (Re-TMS11)

MCM-41 (0.5 g) (XRD (100) 39.9 Å, B.E.T. surface area of 997 m$^2$/g, BJH adsorption pore size of 27.4 Å, 1.5% Nb by weight dopant) was degassed at 600° C. under reduced pressure (10$^{-2}$ torr) for 6 h. The degassed material was loaded together with [Re{h—C$_5$(CH$_3$)$_5$}(CO)$_3$] (0.25 g, 0.6 mmol) in a pyrolysis tube in which the solids were separated by a 10 cm glass wool layer. The reaction vessel was placed in a tube furnace and it was ensured that the volatile rhenium complex and the MCM-41 material were fully exposed to the heat process. After heating the materials at 150° C. (ramp 1.0° C./min) for 3 h under reduced pressure (10$^{-2}$ torr), a gray solid was isolated. The resulting material exhibited IR-active n(CO) absorption at 2013 and 1911 cm$^{-1}$. Reduction of the material under a stream of hydrogen at 300° C. for 3 h gave a gray powder, designated Re-TMS11. The XRD spectrum showed a (100) peak at 38.0 Å, distinct (110) and (200) peaks. Elemental analysis gave 1.0% C; <0.1% H; <0.05% N; and 2.5% Re by weight.

EXAMPLE 17

General Procedure for Heck Olefination of Aryl Halides

A 250 mL three-necked flask, equipped with a thermometer and a reflux condenser was charged with aryl halide (49 mmol), styrene (6.9 mL, 60 mmol) or butyl acrylate (8.6 mL, 60 mmol), triethylamine (7.3 mL, 52.4 mmol), dodecane (7.2 mL, 31.7 mmol) and N,N-dimethylacetamide (48 mL). The palladium catalyst (Pd-GMM) was added through a funnel and the reaction mixture heated to the elevated temperature (mol % of the used catalyst, reaction time and temperature are shown in Table 1). To monitor the reaction, 0.2 mL samples were taken in regular intervals, diluted with N,N-dimethylacetamide and filtered over a bed of Celite, and analyzed by gas chromatography and mass spectrometry (GC/FID, GC/MS). After the completion of the reaction, the mixtures were quenched with H$_2$O(400 mL) and the organic products extracted with diethyl ether (3×200 mL). The combined organic phases were dried over MgSO$_4$, filtered, and concentrated under reduced pressure. The separation of the e/z- isomers was carried out by chromatography on silica gel using pentane/diethyl ether solvent mixtures as the eluent. Recrystallization of the resulting material from concentrated diethyl ether solutions at low temperature afforded an analytically pure product. The catalyst was recovered from the water phase by filtration.

TABLE 1

Heck olefination[a] of aryl halides over Pd-TMS11 catalysts.

| Vinyl substrate | Aryl halide substrate[b] | Amount of catalyst (mol %) | T (° C.) | Time | % Conversion[c] % (Yield)[d] | E:Z | TON[e] |
|---|---|---|---|---|---|---|---|
| Styrene | C$_6$H$_5$Br | 0.1 | 170 | 48 h | 39 (82) | 99:1 | 200 |
| | 4-BrC$_6$H$_4$NO$_2$ | 1.0 | 120 | 20 min | 99 (98) | 95:5 | 50 |
| | 4-BrC$_6$H$_4$NO$_2$ | 0.1 | 120 | 8 h | 98 (99) | 96:4 | 500 |
| | 4-BrC$_6$H$_4$C(O)CH$_3$ | 0.1 | 120 | 45 min | 99 (98) | 95:5 | 1000 |
| n-Butyl Acrylate | C$_6$H$_5$Cl | 0.1 | 170 | 32 h | 16 (40) | 99:1 | 64 |
| | C$_6$H$_5$Br | 0.1 | 170 | 48 h | 67 (92) | 99:1 | 624 |
| | 4-BrC$_6$H$_4$NO$_2$ | 0.1 | 120 | 90 min | 100 (99) | 99:1 | 1000 |
| | 4-BrC$_6$H$_4$C(O)CH$_3$ | 0.02 | 120 | 60 min | 100 (99) | 99:1 | 5000 |

[a]All reactions are carried out in air.
[b]1.1 equiv. of base [N(CH$_2$CH$_3$)$_3$] with respect to the aryl halide substrate is added to the reaction mixture.
[c]Conversion of reactant/determined by gas chromatography.
[d]Mol of coupling product (E + Z)/mol reactant converted.
[e]TON = (mol product)(mol catalyst)$^{-1}$.

EXAMPLE 18

Characterization of the Synthesized Materials

MCM-41 has been prepared using a modified procedure to that reported,[3] giving materials with surface areas of 950–1050 m$^2$/g (BET) and pore diameters of 24–28Å. The palladium grafting of the degassed MCM-41 material (6 h, 600° C., 10$^{-2}$ torr) was carried out via two different methods: sublimation of the volatile organometallic complex [Pd(h—C$_5$H$_5$)(h$^3$—C$_3$H$_5$)] under vacuum through the porous material, or evaporation of the palladium complex into a stream of argon gas that is passed through the porous MCM-41 material. After the palladium complex is deposited onto the inside walls of the pores, the material is reduced under a stream of hydrogen gas at 300° C. for 3–6 h, giving an air stable, black powder.

The preparation of the all samples have been carried out, employing volatile complexes for the introduction of catalytically active precursors, followed by reduction (hydrogen or hydrogen sulfide) or oxidation (air). In some of the selected examples the deposited precursor was transformed into the oxidized species (Cr—, Co—, Zr—, Y—, Sc—, Re-TMS10) via calcination at elevated temperatures in air or as in the case of MOS-TMS10, hydrogen sulfide gas was used as a reductant.

Figure 3:
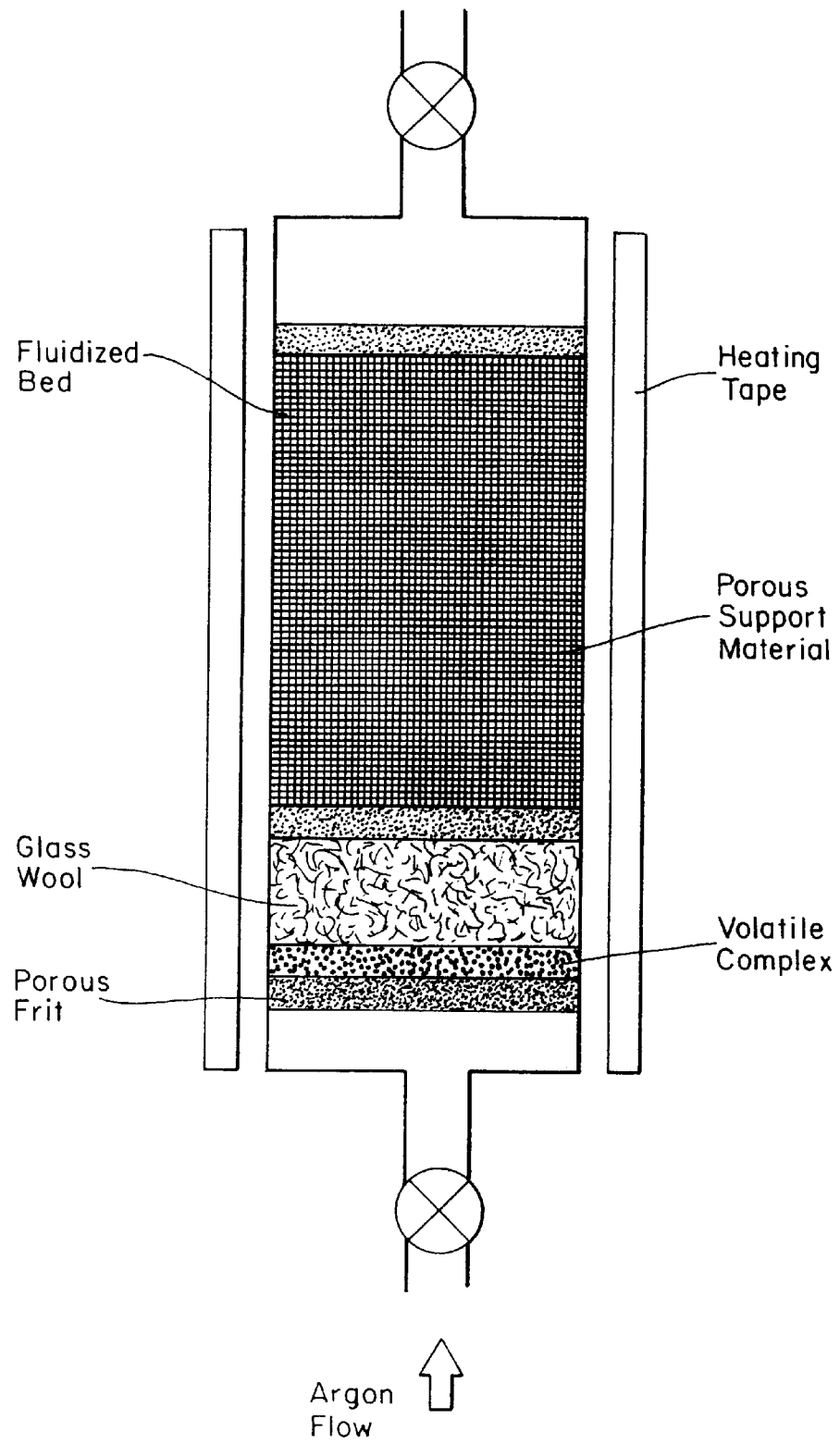
FIG. 3 shows a fluidized bed reactor for the vapor-depositing process.
Figure 4:
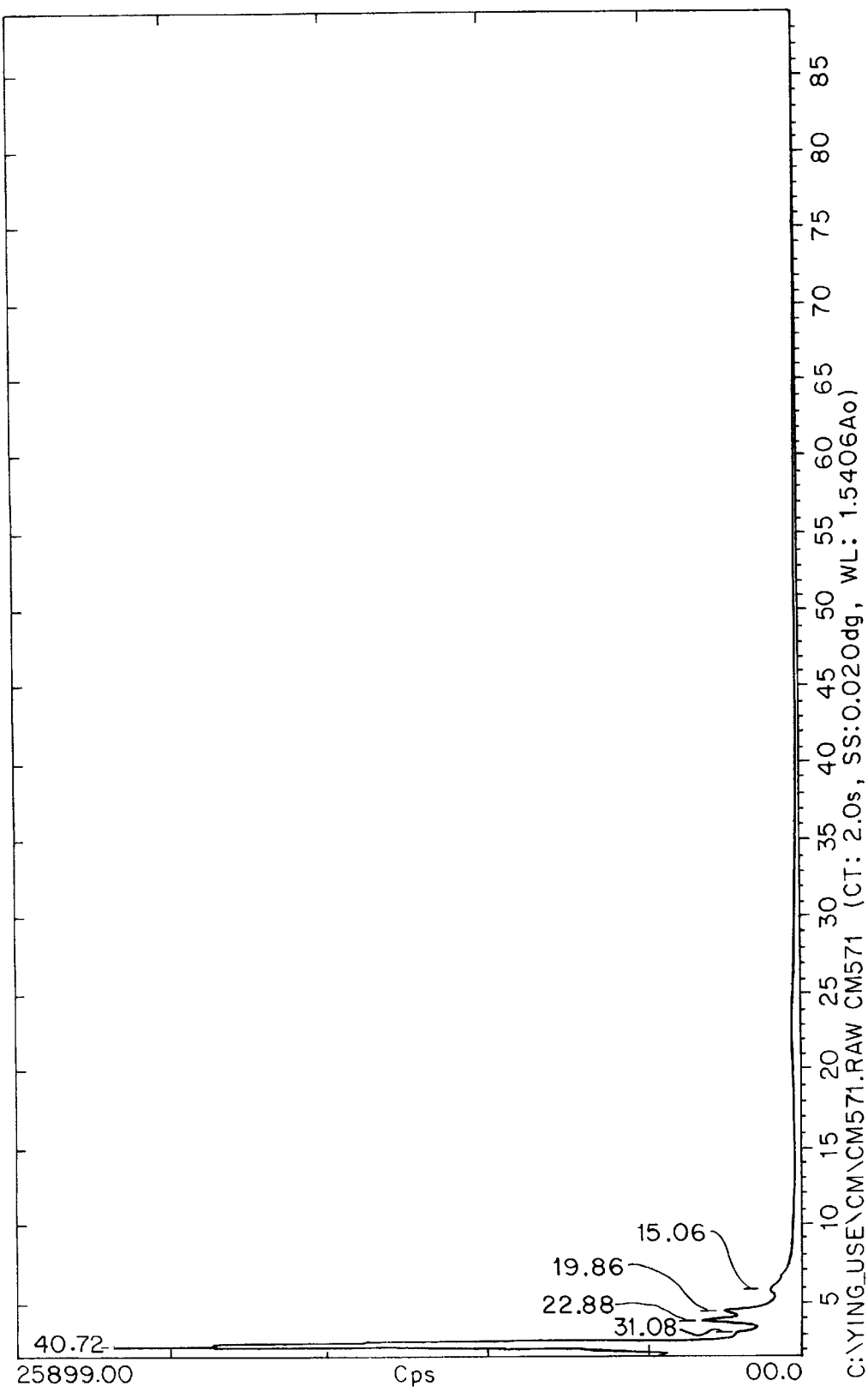
FIG. 4 is an x-ray diffraction (XRD) pattern of MCM-41.
Figure 5:
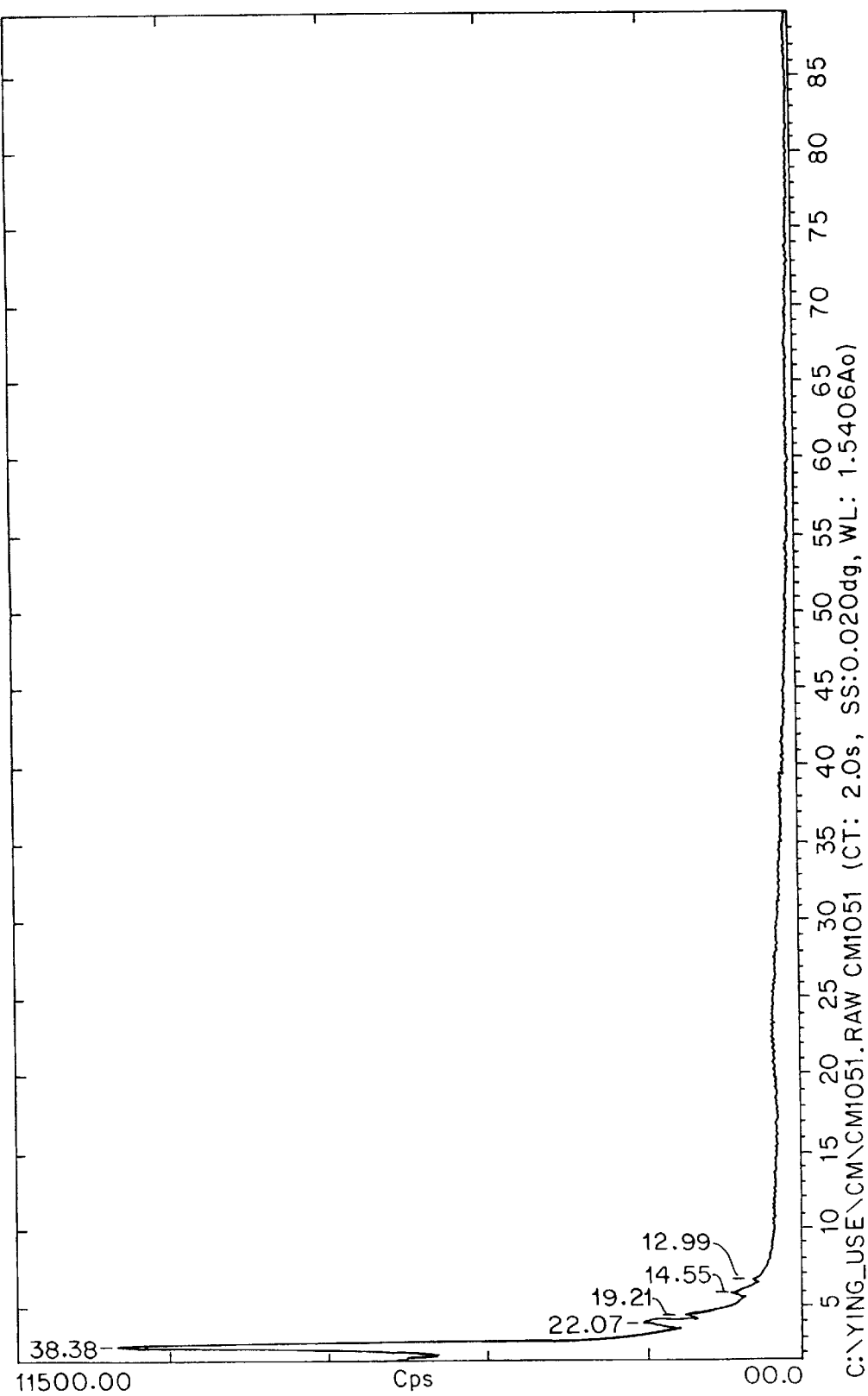
FIG. 5 is an XRD pattern of Pd-TMS11.
Figure 9:
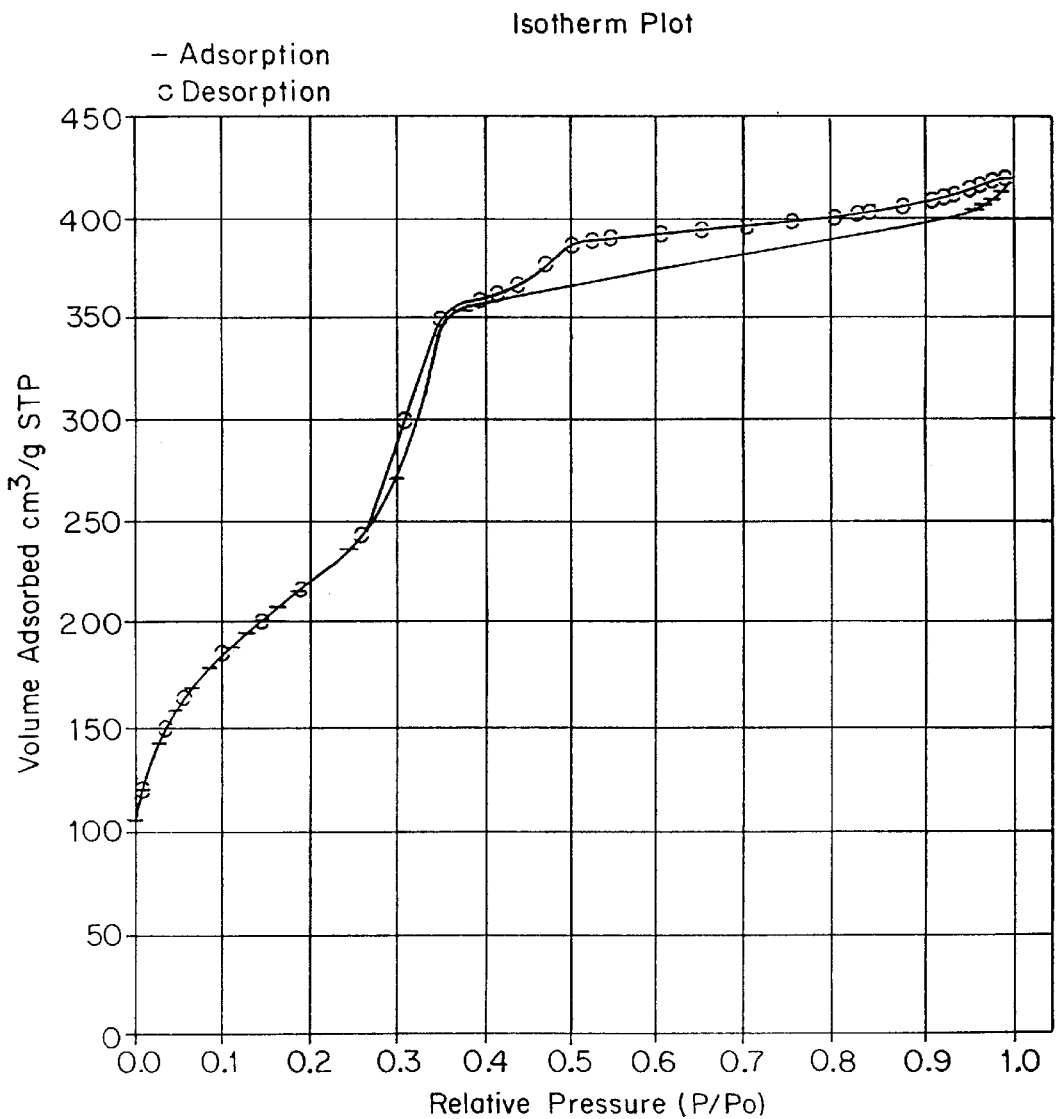
FIG. 9 shows the BET surface area of a typical sample of Pd-TMS11.
Figure 10:
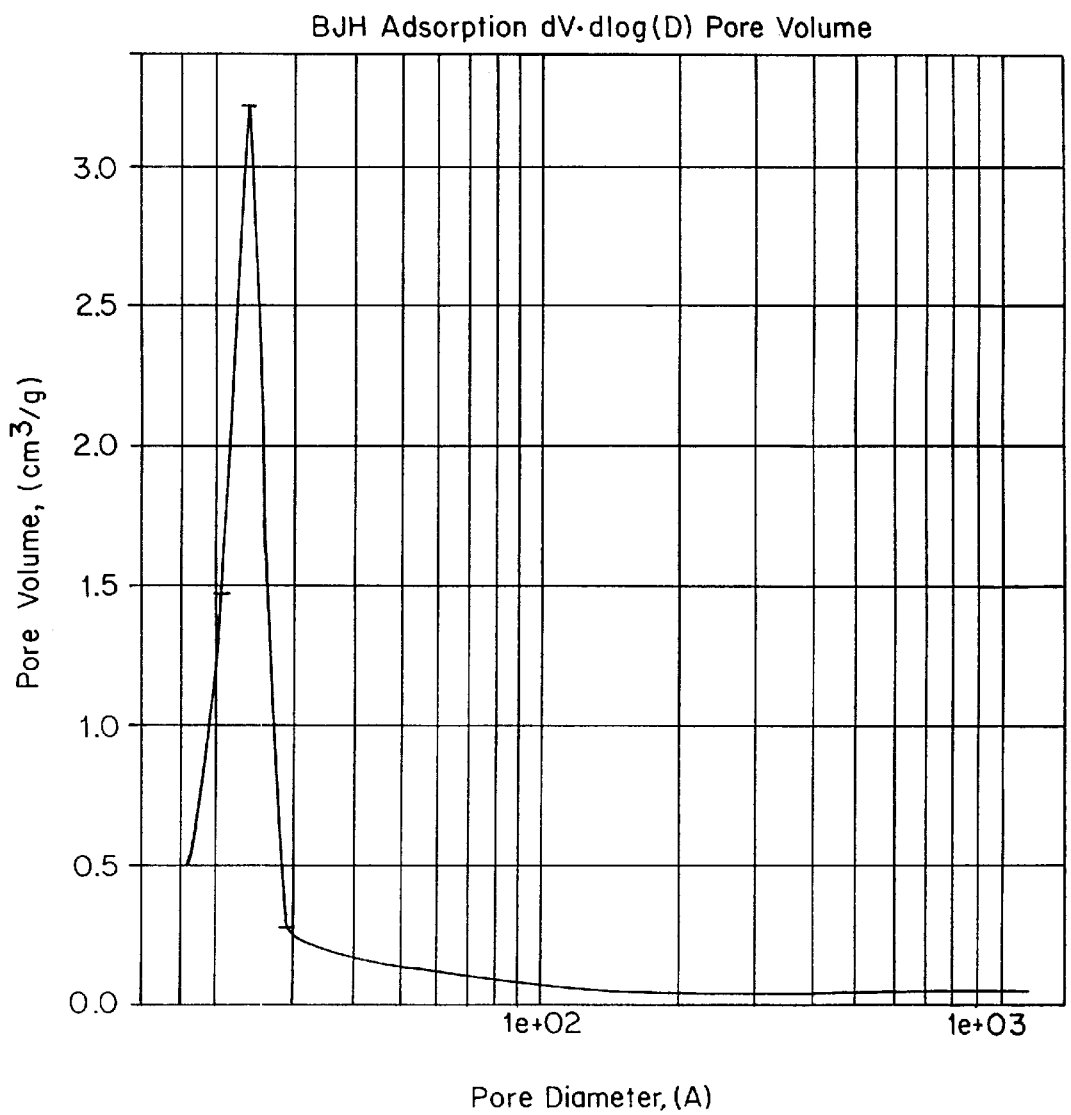
FIG. 10 shows BJH pore size distribution of Pd-TMS11.

All the materials have been characterized by XRD, surface area analysis and microanalysis as stated in the Experimental Section. In addition, all samples have been investigated using transmission electron microscopy (TEM) and EDAX analysis (EDAX=Energy Dispersive Analysis by X-ray). The characterization data obtained for Pd-TMS11 is described below as a representative example. The prepared catalyst, Pd-TMS11, retains its hexagonally-packed porous structure as shown by the X-ray diffraction (XRD) pattern (FIG. 5). Although the diffraction patterns of Pd-TMS11 and the MCM-41 starting material (FIG. 4) are almost identical, the peak intensity for Pd-TMS11 is strongly reduced due to radiation diffusion caused by the grafted palladium metal. The XRD pattern of palladium metal has major diffraction peaks at 2q=40.1° (111) and 46.70 (200), which are not found in the XRD spectrum of Pd-TMS11, indicating that the palladium metal is highly dispersed in the latter. Further evidence is provided by transmission electron micrographs (TEM) that show the hexagonally-packed pore structure in Pd-TMS with no noticeable palladium clusters (FIGS. 7(a), 7(b)). In addition, Energy Dispersive Analysis by X-ray (EDAX) studies have been conducted on Pd-TMS11 particles, indicating that palladium is uniformly dispersed over the pore surface of the mesoporous support (FIG. 8). Elemental analysis of Pd-TMS11 samples shows palladium metal contents between 10–30wt %, depending on the amount of volatile complex [Pd(h—$C_5H_5$)($h^3$—$C_3H_5$)] used in the vapor grafting process. To achieve lower palladium loading, surface modified MCM-41 was applied. BY using silane reagents, it was possible to deactivate surface-bound oxygen groups and therefore reduce the amount of anchor positions for the volatile organometallic palladium precursor. Depending on the residual amount of surface-bound oxygen groups and the amount of palladium precursor, the metal content can be adjusted between 1–10 wt %. For the scale-up of the catalyst production a fluidized bed reactor was utilized (FIG. 3). In the preparation, the porous support material was kept in a stream of inert gas which was saturated with the volatile grafting agent to ensure the uniform metal grafting of the support. This reactor set-up enabled the multi-gram synthesis of vapor-grafted TMS11 materials. The B.E.T. surface area of a typical sample of Pd-TMS11 (FIG. 9) with a palladium content of 19.1 wt % is at 750 m$^2$/g. The BJH pore size distribution of Pd-TMS11 (FIG. 10) indicates a narrow peak centered at 26 Å for the pore diameter which is smaller than that determined for the MCM-41 starting material (27.4 Å) due to the grafted palladium metal. The CO adsorption studies of Pd-TMS11 show metallic surface areas between 116 and 140 m$^2$/g$_{(pd\ metal)}$ with a metal dispersion of more than 30%. In comparison, commercially available palladium on Pd/g-Al$_2$O$_3$ (Aldrich) shows a metallic surface area of only 65 m$^2$/g$_{(pd\ metal)}$ with a metal dispersion of only 15%.

EXAMPLE 19

Catalytic Study of Pd-TMS11 in Heck Reactions

Figure 11:
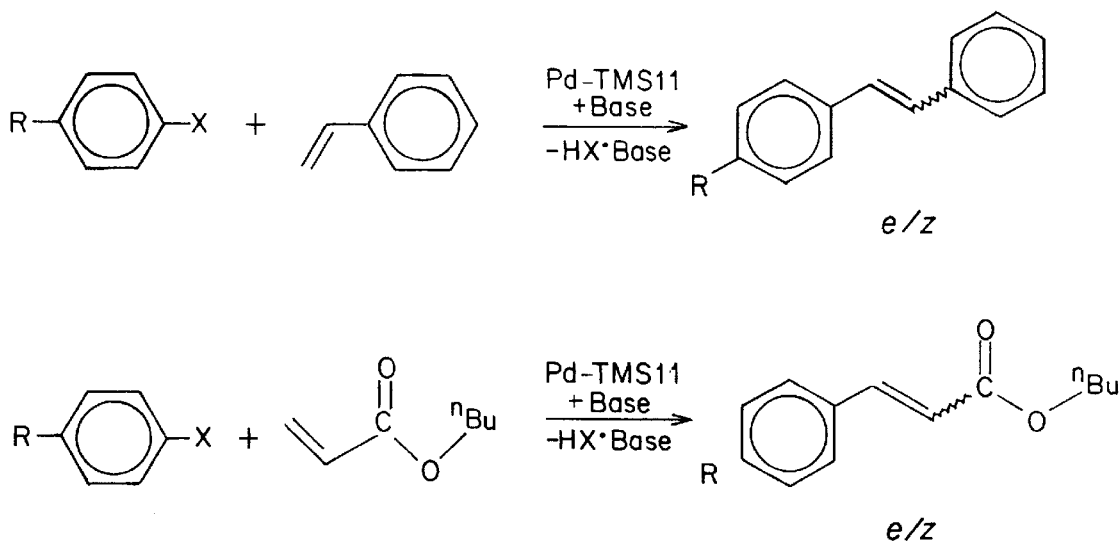
FIG. 11 shows a reaction scheme of Heck carbon-carbon coupling reaction of aryl halides.

The Pd-TMS11 materials catalyze the Heck carbon-carbon coupling reaction of aryl halides (FIG. 11). The catalytic activity of these materials was investigated using activated and non-activated aryl halides with styrene and butyl acrylate as the vinylic substrate (Table 1). The yields for the activated aryl halides, with respect to reaction time and amount of catalyst, showed that the Pd-TMS11 catalysts have an outstanding activity and represent one of the most active Heck catalysts. Quantitative conversion and a yield of 100% was obtained after only 1 h for the reaction of n-butyl acrylate and 4-bromoacetophenone using as little as 0.02 mol % catalyst. The Pd-TMS11 material therefore provides an extremely simple and efficient Heck catalyst that rivals or even surpasses the best homogeneous catalyst in use today. A moderate conversion of bromo- and chlorobenzene was observed, and a conversion of 67% for bromobenzene has been achieved.

Figure 6:
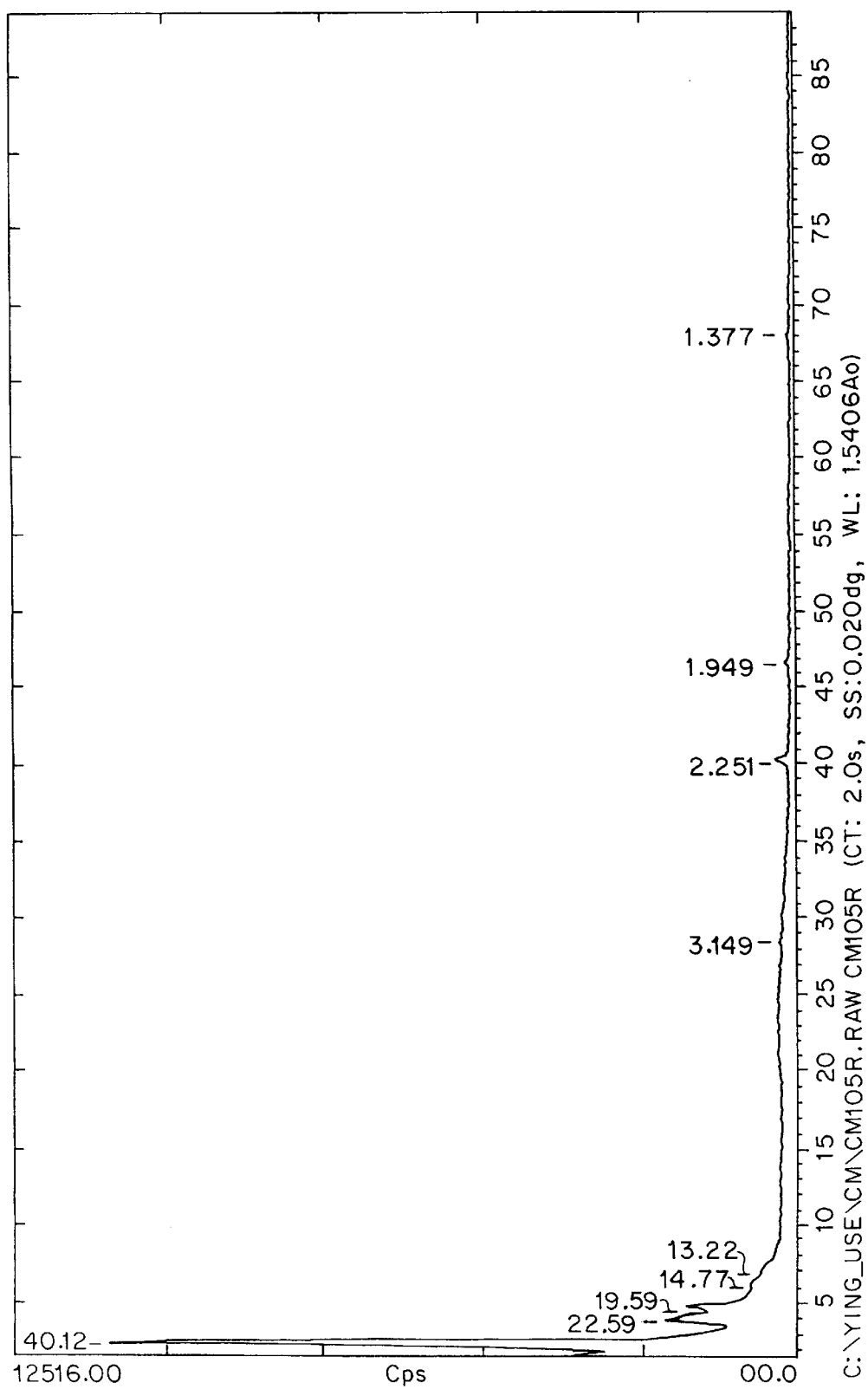
FIG. 6 is an XRD pattern of a recovered catalyst Pd-TMS11 after a catalytic reaction has taken place.
Figure 8C:
Figure 8B:
Figure 8E:
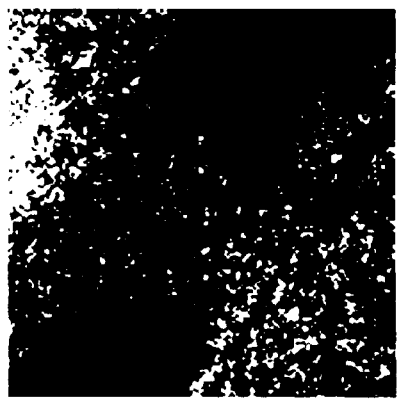
Figure 8A:
Figure 8D:
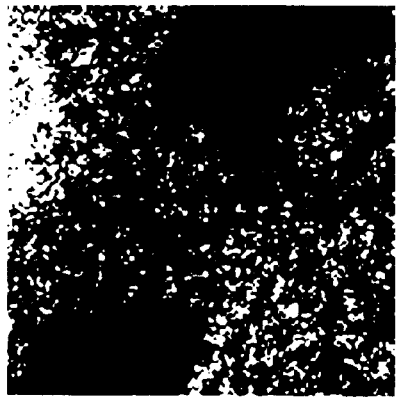

One particular advantage of the Pd-TMS11 material is that the catalysis experiments could be conveniently carried out in air, and the separation of the heterogeneous catalyst could be simply achieved by filtration. The recovered catalyst retains its porous structure, as it is apparent in the XRD pattern (FIG. 6). In addition, the spectrum shows three weak peaks at 2q=40.1 and 46.70 that correspond to palladium metal, indicating the formation of palladium clusters. Investigation of the recovered Pd-TMS11 catalyst by transmission electron microscopy showed some palladium agglomeration and partial degradation of the palladium grafted molecular sieve. The support material retained a very high B.E.T. surface area (782 m$^2$/g) with a narrow pore size distribution after the reaction. The recovered Pd-TMS11 catalyst can be further re-used for Heck reactions.

EXAMPLE 20

Titanium Nitride Grafted MCM-41 (TIN-TMS11)

MCM-41 (0.3 g) (XRD (100) 40.2 Å, B.E.T. surface area of 845 m$^2$/g, BJH adsorption pore size of 21.5 Å) was degassed at 600° C. under reduced pressure (10$^{-2}$ torr) for 6 h. The resulting material was loaded into a short path frit and contained with glass wool under an inert gas atmosphere. A small round-bottom flask was filled with [Ti{N(CH$_3$)$_2$}$_4$] (1.7 g, 7.6 mmol) and was connected to the prepared frit that was further attached to a condensation bridge with a round-bottom flask. The apparatus was evacuated and a constant pressure (10$^{-2}$) torr) was maintained by cooling the empty round bottom flask to −196° C. The small round-bottom flask containing the volatile titanium complex and the loaded frit were heated to 75° C. (ramp 1° C./min) using an oil bath. During the heating process, the white MCM-41 starting material turned pink and the excess volatile organometallic complex was condensed into the cooled round-bottom flask. The resulting solid was treated in a stream of ammonia gas at 250° C. for 6 h, giving a yellow powder designated TiN-TMS11. The XRD spectrum showed a (100) peak at 40.2 Å, and analysis of the surface area by the B.E.T. method gave 701 m$^2$/g with a BJH adsorption pore size of 21.5 Å. Elemental analysis gave 13.0% Ti and 2.4% N by weight.

What is claimed is:
1. A method comprising:
    volatilizing an inorganic compound; and
    allowing the inorganic compound to become immobilized on a porous oxygen-containing substrate having an average pore size of at least about 8 Å, wherein immobilization occurs to an extent that the inorganic compound remains immobilized on the substrate under sublimation conditions.

2. A method as in claim 1, further comprising:

pretreating a substrate having a plurality of chemically active sites of a first chemical functionality such that about 1–25% of the sites retain the first chemical functionality and about 75–99% of the sites have a second functionality, wherein the sites retaining the first chemical functionality are uniformly dispersed, wherein the volatilizing causes the inorganic compound to become immobilized on the pretreated substrate.

3. A method as in claim 2, wherein the pretreating step comprises reacting the substrate with a compound having a formula $R_3SiX$, wherein R is selected from the group consisting of $C_1$–$C_{10}$ alkyl, and aryl and X is selected from the group consisting of halide and $C_1$–$C_6$ alkoxide.

4. A method as in claim 2, wherein the pretreating step comprises subjecting the substrate to a vacuum of at least $10^{-2}$ torr and heating the surface to a temperature of less than about 800° C.

5. A method as in claim 1, wherein the inorganic compound and substrate have a general formula:

SUBSTRATE —O—M—$L_x$ wherein M is a metal ion, L is a ligand and x is at least 1.

6. A method as in claim 5, wherein a bond between O and M is a covalent bond.

7. A method as in claim 1, wherein the inorganic compound loses no more than about 50% of its surface area during the allowing step.

8. A method as in claim 1, further comprising allowing the immobilized inorganic compound to decompose to a metal compound.

9. A method as in claim 8, wherein the metal compound is selected from the group consisting of metal, metalloid, inorganic complex, metalloid complex, metal oxide, metal nitride, metal sulfide, metal carbide, metal halide and a combination thereof.

10. A method, comprising:

performing a carbon-heteroatom coupling reaction involving the metal compound of claim 8.

11. A method as in claim 10, wherein the carbon-heteroatom coupling reaction is performed in air, and at least about 5% conversion is achieved within 1 h.

12. A method as in claim 10, wherein the carbon-heteroatom coupling reaction is selected from the group consisting of carbon-carbon coupling reactions and carbon-nitrogen coupling reactions.

13. A method as in claim 12, wherein the carbon-heteroatom coupling reaction is a carbon-carbon coupling reaction.

14. A method as in claim 13, wherein the carbon-carbon coupling reaction is a Heck reaction.

15. A method as in claim 1, wherein the substrate has a surface area of at least about 10 $m^2/g$.

16. A method of performing a carbon-heteroatom coupling reaction, comprising: carrying out a carbon-heteroatom coupling reaction catalyzed by a surface-immobilized catalyst prepared by the method of claim 1 having a surface area of at least about 50 $m^2/g$, in air, at a temperature of at least 50° C., while allowing catalyst degradation, defined by a reduction of catalytic activity, of less than about 30% over a period of time of at least about 1 h.

17. A method as in claim 1, wherein the porous substrate has a porosity volume of at least about 5%.

18. A method as in claim 1, wherein the substrate is a metal oxide material, the metal being selected from the group consisting of alkali metals, alkaline earth metals, transition metals, main group metals, lanthanides, and actinides.

19. A method comprising:

volatilizing an inorganic compound; and allowing the inorganic compound to become immobilized on a porous oxygen-containing substrate having an average pore size of at least about 8 Å, wherein immobilization occurs to an extent that the compound is not removable from the substrate under conditions of reflux in a solvent in which the compound is soluble.

20. An article comprising a porous substrate having an average pore size of at least about 8 Å and a vapor-deposited metal compound immobilized on the substrate.

21. An article as in claim 20, wherein an article has a surface area of at least about 40 $m^2/g$.

22. An article as in claim 20, further comprising the structure:

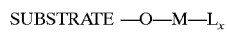

SUBSTRATE —O—M—$L_x$ wherein a bond between O and M is a covalent bond, L is a ligand and x is at least 1.

23. An article as in claim 20, wherein the article has a surface area of at least 10 $m^2/g$.

24. A method as in claim 20, wherein the porous substrate has a porosity volume of at least about 5%.

* * * * *

UNITED STATES PATENT AND TRADEMARK OFFICE
CERTIFICATE OF CORRECTION

PATENT NO. : 6,489,258 B1
DATED : December 3, 2002
INVENTOR(S) : Ying et al.

It is certified that error appears in the above-identified patent and that said Letters Patent is hereby corrected as shown below:

Column 1,
Line 20, just before the BACKGROUND OF THE INVENTION, please insert
-- This invention was made with government support under Contact Number 9257223-CTS awarded by the National Science Foundation. The government has certain rights in this invention. --

Signed and Sealed this

Twenty-fifth Day of March, 2003

JAMES E. ROGAN
*Director of the United States Patent and Trademark Office*